(12) United States Patent
Keeve et al.

(10) Patent No.: US 9,239,300 B2
(45) Date of Patent: Jan. 19, 2016

(54) X-RAY SYSTEM AND METHOD FOR GENERATING 3D IMAGE DATA

(75) Inventors: Erwin Keeve, Potsdam (DE); Fabian Stopp, Berlin (DE); Eckart Uhlmann, Kiebitzreihe (DE)

(73) Assignees: Fraunhofer-Gesellschaft zur Förderung der angewandten Forschung e.V., München (DE); Charité—Universitätsmedizin Berlin, Berlin (DE)

( * ) Notice: Subject to any disclaimer, the term of this patent is extended or adjusted under 35 U.S.C. 154(b) by 438 days.

(21) Appl. No.: 13/643,927

(22) PCT Filed: Apr. 21, 2011

(86) PCT No.: PCT/EP2011/002167
§ 371 (c)(1),
(2), (4) Date: May 14, 2013

(87) PCT Pub. No.: WO2011/134676
PCT Pub. Date: Nov. 3, 2011

(65) Prior Publication Data
US 2013/0230137 A1    Sep. 5, 2013

(30) Foreign Application Priority Data

Apr. 26, 2010 (DE) .......................... 10 2010 018 627

(51) Int. Cl.
*G01N 23/04* (2006.01)
*A61B 6/00* (2006.01)

(52) U.S. Cl.
CPC .............. *G01N 23/04* (2013.01); *A61B 6/4405* (2013.01); *A61B 6/4458* (2013.01); *A61B 6/4476* (2013.01); *A61B 6/547* (2013.01); *A61B 6/583* (2013.01)

(58) Field of Classification Search
CPC ...... G01N 23/04; A61B 6/022; A61B 6/4441; A61B 6/466; A61B 6/12; A61B 6/032; A61B 6/469; A61B 6/502; A61B 6/4405; A61B 6/4458; A61B 6/547; A61B 9/5244; A61B 6/5247; A61B 6/08; A61B 6/4233; A61B 6/488; A61B 2019/5251; A61B 2019/5255; A61B 5/1114; A61B 19/26; A61B 19/5244; A61B 1/0005; A61B 2019/528; A61B 2019/52; A61B 6/4476; A61B 6/583; H04N 13/0221; H04N 13/0239; H04N 13/006; G01B 11/2513; G01B 11/2518; G01B 11/25; G01B 21/10; G01B 21/18; G01B 5/12; G01B 5/18; G01B 11/002; G01B 11/24; G01B 11/2531; G01B 11/2545
USPC ................................................. 378/41, 102
See application file for complete search history.

(56) References Cited

U.S. PATENT DOCUMENTS 6,862,337 B2 *   3/2005  Claus et al. ..................... 378/26
2004/0170254 A1  9/2004  Gregerson et al.

(Continued)

FOREIGN PATENT DOCUMENTS

WO    WO2010012441    2/2010

OTHER PUBLICATIONS

International Search Report for PCT/EP2011/002167 dated Jan. 31, 2012, 2 pages (translated).

*Primary Examiner* — Irakli Kiknadze
(74) *Attorney, Agent, or Firm* — Reising Ethington P.C.

(57) ABSTRACT

The present invention relates to an X-ray system and method for generating 3D image data. The X-ray system comprises a radiation detector, a movable X-ray tube assembly and a control unit, wherein in a working state of the system the radiation detector is detachably positioned in a spatially fixed manner and the X-ray tube assembly can be moved into relative positions relative to the radiation detector. Projection images recorded in the relative positions can be processed together with the coordinates of the relative positions using an iterative reconstruction technique or other image processing methods so as to obtain 3D X-ray images. The X-ray tube assembly is attached to a motor-driven movable stand arm and can be displaced using a control unit. The stand base of the movable stand can be positioned in a spatially fixed manner, so that it has a defined fixed position relative to the radiation detector.

14 Claims, 4 Drawing Sheets

(56) References Cited

U.S. PATENT DOCUMENTS

| | | |
|---|---|---|
| 2008/0013692 A1 | 1/2008 | Maschke |
| 2008/0024488 A1* | 1/2008 | Visser .................. A61B 6/466 345/420 |
| 2008/0285712 A1 | 11/2008 | Kopans et al. |
| 2009/0074151 A1* | 3/2009 | Henderson et al. .......... 378/198 |
| 2010/0067660 A1* | 3/2010 | Maurer .................. A61B 6/12 378/95 |
| 2010/0189226 A1* | 7/2010 | Kotowski et al. ............. 378/198 |
| 2011/0064193 A1* | 3/2011 | Minnigh ............. A61B 6/4266 378/62 |
| 2011/0075814 A1* | 3/2011 | Boese .................. A61B 6/4007 378/122 |

\* cited by examiner

ND METHOD FOR
X-RAY SYSTEM AND METHOD FOR GENERATING 3D IMAGE DATA

TECHNICAL FIELD

The present invention relates to an X-ray system and to a corresponding method for generating 3D image data.

BACKGROUND

In the medical field, X-ray systems are used to examine patients by means of X-rays, wherein such systems comprise an X-ray source and an X-ray detector. In materials science, objects to be analyzed are likewise radiographed so as to obtain information about the inner structure in a non-destructive manner. The X-rays generated by the X-ray source penetrate the tissue or material to be represented and are weakened to varying degrees, depending on the tissue type or material type. A projection image of the transilluminated object, in which spatial information is displayed in a superimposed manner, is created on the X-ray image detector of an X-ray device. However, it is only a three-dimensional exact representation of the interior of the body that allows, for example, exact repositioning of bone fractures on joints or exact positioning of implants relative to critical anatomic structures.

So as to generate three-dimensional image data, several two-dimensional projection images of an object are recorded from various spatial directions by means of an X-ray device and then the scanned volume is reconstructed using an algorithm. In addition to the 2D projection images, the algorithm requires positional information for the X-ray tube assembly and radiation detector, and additionally it must be taken into consideration that the object to be reconstructed is always represented in the projection images.

Several methods and devices for generating three-dimensional X-ray images are already known from the prior art. Often times what are known as "C-arms" are employed for this purpose, as described in WO 2010/012441 A1, for example. While these C-arms allow the scanned region to be reliably reconstructed, and the image quality is sufficient for intraoperative purposes, a surgeon has no direct access to the patient's entire body with these devices due to the shape thereof.

Computer tomographs make an excellent image quality possible, but are not suitable for intraoperative use, because the device blocks the access to the patient. Such devices additionally require a lot of space, generate high radiation exposure, are complex to operate and cause high costs.

SUMMARY

It is thus an object of the present invention to develop an X-ray system which avoids the aforementioned drawbacks, which is to say which can be used to generate reproducible 3D X-ray images with lower radiation exposure, while the object to be represented is not enclosed by the device and the images can be recorded in random positions.

This object is achieved according to the invention by an X-ray system and by a method for operating the same.

The x-ray system comprises an radiation detector and a movable X-ray tube assembly, which are required for imaging purposes, and a control unit for operating the system. In the working state of the system, the radiation detector is positioned in a spatially fixed manner, however it can be detached from this position. The radiation detector can thus be attached in several locations, which together with the mobility of the X-ray tube assembly increases the variability of the system. The spatially fixed radiation detector defines a locally fixed coordinate system, and the X-ray tube assembly moves relative to the radiation detector in various relative positions for recording X-ray projection images. Because of the position and orientation of the X-ray tube assembly, the assembly defines a reference coordinate system, which is fixed in terms of the body and which, by way of transformation, can be converted into the locally fixed coordinate system, relative to the locally fixed base coordinate system, whereby the relative positions in the two coordinate system are clearly defined. Using the X-ray projection images recorded in these relative positions and the coordinates of the relative positions, 3D X-ray images can be calculated by way of iterative reconstruction technique or other image processing methods.

For mobile and intraoperative use, the system comprises a movable stand having a motor-driven movable stand arm and a stand base. The X-ray tube assembly is attached to the stand arm and can be moved in at least four degrees of freedom. These four degrees of freedom are required to obtain X-ray projection images having the necessary depth of information for reconstructing a three-dimensional representation. These degrees of freedom preferably comprise three translatory degrees of freedom so as to be able to scan the entire object to be represented and carry out the scan process at various heights above the object. In addition, a rotatory degree of freedom is required in this case, so as to be able to rotate the X-ray tube assembly in the various positions which can be achieved by way of the translatory movement in the direction of the volume of the object to be represented, and thus acquire this volume under a different angle. It is decisive for this purpose that the X-ray tube assembly remains directed at the radiation detector at all times. As an alternative, for example, only one translatory movement having two degrees of freedom in a plane parallel to the radiation detector and tilting of the X-ray tube assembly by two rotatory degrees of freedom, which is to say by two angles, may be provided.

The stand base is positioned likewise in a spatially fixed manner by way of means of fastening devices and thus has a fixed distance relative to the radiation detector and a fixed position within the locally fixed base coordinate system. The stand allows the system to be freely positioned, so that a physician has access to the patient's body even during surgery. The stand arm can likewise be moved freely and is easy to move out of the working range of the physician during surgeries and moved back into a recording position for new images. The joints of the stand arm are equipped with absolute measurement transmitters of the joint positions, so that it is possible to reproducibly move into positions and establish orientations of the X-ray tube assembly by means of the motor-driven actuation of the stand arm. It is thus possible to reproducibly record images of particular regions and compare them to each other with regard to changes, such as the introduction of an implant.

Advantageous refinements of the system will be described in the dependent claims.

According to one advantageous refinement, the stand base comprises sensors for ensuring that the spatially fixed position of the stand base is maintained. Because 3D X-ray imaging is only reliable and reproducible if the position of the stand base is always spatially fixed in relation to the radiation detector, sensors in the stand base can, for example, measure the distance from a patient table or other spatially fixed objects, such as lamps, and output a warning on a display unit in the event of variances from the predetermined distance.

The system can further comprise sensors, for example motion detectors, which monitor particular areas for the presence of people. Because the radiation exposure should be minimized for all persons involved in the examination, these sensors can detect whether persons are still in the room during recording, or may even be present in the recording range of the X-ray tube assembly, and then interrupt the recording procedure and output an error message via the display unit. This excludes inadvertent operation of the X-ray system. It can further be detected, for example, whether a patient wakes up prematurely from anesthesia and moves out of the recording region, whereby unnecessary radiation exposure for the patient due to needless X-ray images is avoided.

In an advantageous refinement, the aforementioned sensors comprise lasers by means of which distances between objects or even movements can be detected with very high precision.

The X-ray tube assembly may also be movable in five degrees of freedom, which results in greater variability of the orientation thereof relative to the object to be represented. In a particularly advantageous manner, the X-ray tube assembly can be moved in six degrees of freedom, which is to say in all three translatory and all three rotatory degrees of freedom.

According to a further advantageous refinement, position sensors, for example gyroscopes, or acceleration sensors, for determining the relative position of the X-ray tube assembly with regard to the base coordinate system may be present in the X-ray system. In addition to the position determination via the joint positions of the stand arm, a second position determination option thus exists, which increases the accuracy of the position determination.

So as to spatially fix the stand base, wheels, which otherwise are used to move the base freely in the space, can be blocked or the stand can be held on the floor by means of vacuum suction. Fixing the base is important for reconstructing the three-dimensional images, because the key here is an unchanged relative position between the radiation detector and X-ray source since the calibration.

According to a further advantageous refinement, the radiation detector can be detachably positioned in a spatially fixed manner by holding devices. This achieves a spatial fixation of the radiation detector on a plurality of objects such as operating tables, stretchers and the like, wherein the fixation preferably takes place on spatially fixed objects, because in this case the locally fixed coordinate system is determined by way of an immovable fixed point.

In addition to the motor-driven displacement, the stand arm can also be manually adjusted to certain positions, for example to as to set a desired recording track for X-ray projection images using a "teach-in" method.

So as to increase the stability of the X-ray system, the radiation detector can be mechanically connected to the stand by way of an adapter. This always predetermines an exactly defined distance and an exact position within the locally fixed base coordinate system, which cannot be inadvertently modified.

In an advantageous refinement, the X-ray system comprises a positioning unit for the object to be represented, for example an operating table to which the radiation detector is attached, wherein the radiation detector preferably has the same width as the positioning unit that is used (in the present invention, the "same width" shall be understood to mean a variation of the width of the radiation detector and positioning unit of +/−10%). This ensures that the object to be represented can be completely represented on the radiation detector.

As a refinement of the aforementioned X-ray system in the form of a separate invention (which is to say the radiation detector alone, without additional characteristics of the aforementioned X-ray system), the radiation detector comprises several individual detectors, which can be combined by means of joints and detent elements to form a folding or telescopic detector system. In addition to a mechanical connection, the joints and detent elements also establish an electrical connection between the individual detector plates. As an alternative, the individual detector plates can be connected via separate electrical cables to the remainder of the system. The detector can thus be compressed in a space-saving manner by folding in the detector plates against each other or displacing them beneath each other. The object to be examined can thus be accessed more easily so as to carry out modifications. In order to record additional X-ray images, the radiation detector is folded out or extended to the full length or width and thus allows greater variability of the X-ray images, because a larger angular range can be recorded due to an increased detector surface.

The method for using the described X-ray system comprises as a first step a calibration of the system, with the radiation detector being spatially fixed and the stand base being spatially fixed, by means of a calibration body. The calibration body is attached between the X-ray tube assembly and radiation detector for this purpose, but is preferably directly connected to the radiation detector. The calibration body has a predetermined structure made of material that weakens X-rays, for example a metal lattice. At least one X-ray projection image of the calibration body is recorded, and based on this projection image, or based on these projection images, and the known geometry of the three-dimensional calibration body, it is then possible to determine the position and orientation of the radiation detector relative to the base coordinate system defined by the position of the radiation detector.

After the calibration has been completed, the calibration body is removed and the object to be represented is introduced in place thereof between the X-ray tube assembly and radiation detector. Several X-ray projection images are now recorded of the object to be represented in arbitrary relative positions, which are used to create a three-dimensional reconstruction of the volume region penetrated by radiation using an iterative reconstruction technique by way of the coordinates of the relative positions used for recording. By using an iterative reconstruction technique or other image processing methods, a small number projection images suffices for three-dimensional imaging, and the radiation exposure of the patient is minimized.

According to an advantageous refinement of the method, a "teach-in" method predetermines a recording track for a motor-driven movable arm for recording X-ray projection images. For this purpose, the stand arm having the X-ray tube assembly attached thereto is moved manually into specific relative positions, in which later the projection images are to be taken and which define the recording track. The coordinates of these relative positions are stored in a control unit, and after the manual setting process is completed, the control unit and the motor controller of the stand arm can be used to automatically move into these relative positions, so that projection images can be created automatically along a recording track.

According to a further advantageous refinement of the method, a "teach-in" method is used to predetermine a movement track of the stand arm, together with the X-ray tube assembly, for recording the projection image. Using a defined number of X-ray projection images to be recorded, the optimal positions of the X-ray tube assembly on the recording track are then automatically calculated. Using the control unit and the motor controller of the stand arm, the recording track of the "teach-in" method is followed automatically and X-ray projection images are recorded in the calculated positions.

BRIEF DESCRIPTION OF THE DRAWINGS

Exemplary embodiments of the invention are shown in the drawings and described hereafter based on FIGS. 1 to 3.

In the drawings.

DETAILED DESCRIPTION OF THE ILLUSTRATED EMBODIMENTS

Figure 1:
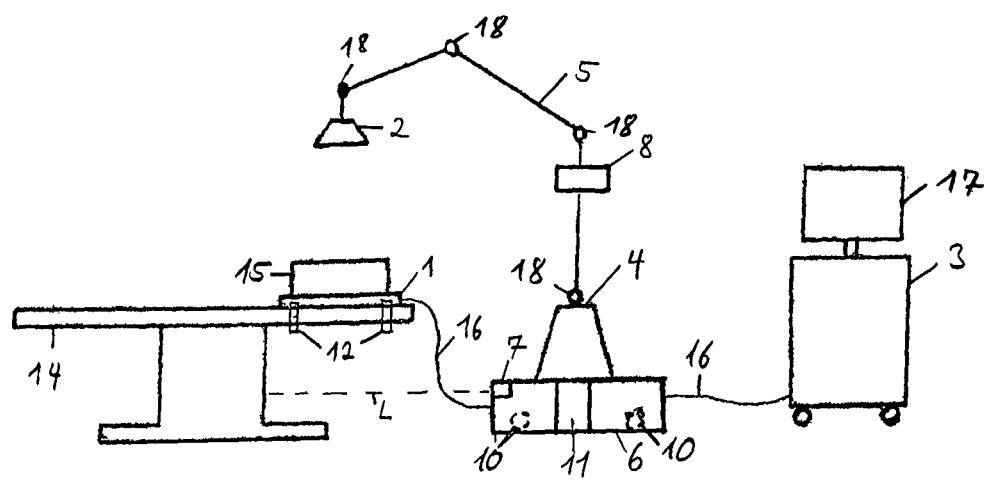
FIG. 1 is a schematic illustration of a side view of the X-ray system with a calibration body.

FIG. 1 shows a side view of a system according to the invention. The radiation detector 1, which contains a scintillator layer converting impinging X-rays into visible light which is detected by light-sensitive electronic elements, rests on a positioning unit 14 for the object to be represented, in this case an operating table made of metal, which is connected to the floor in a spatially fixed manner, and is attached by means of holding devices 12, for example clamps made of plastic material or metal. The holding devices 12 can be detached and the radiation detector 1 can thus be fixed in a different position. Handles, which are not shown here, are provided on the radiation detector 1 for easier transport and for attachment.

A stand 4 is positioned in a spatially fixed manner in that a stand base 6 is held against the floor by a vacuum suction system 11, so that the base can no longer be moved, despite the wheels 10. A movement of the stand base, however, can also be carried out by means of casters or guided on rails. A stand arm 5 is set such that an X-ray tube assembly 2 is located above the calibration body 15 seated on the radiation detector. The components that are required for operating the X-ray tube assembly, such as a high-voltage generator, for example, are not shown in this illustration, but are sufficiently known. The calibration body 15 is made of a wire or ball frame model, wherein the wires or the individual spheres are arranged offset from each other in several planes. In this position, the projection images that are required for calibrating the system can be created. For transmitting the obtained image and supplying power, the radiation detector 1 is connected via an electrical connection 16 to the stand 4 and the stand is connected via an electrical connection to a control unit 3 and a display unit 17. In this example, the control unit comprises a PC, which is connected to a monitor as the display unit 17.

By way of a sensor for distance measurement 7, a laser beam L is used to determine the distance between the base of the positioning unit 14 and the stand base 6 and an error message is output on the display unit 17 in the event of variances. The laser beam L has only low intensity and is guided close to the floor so as not to place people at risk due to exposure. In addition, the wavelength is in the visible range so as to highlight the position of the laser to people involved in the examination. A motion detector 8, which comprises an infrared sensor, registers the presence of people in the room and interrupts the radiography process if people are located in the surroundings of the X-ray system.

Figure 2:
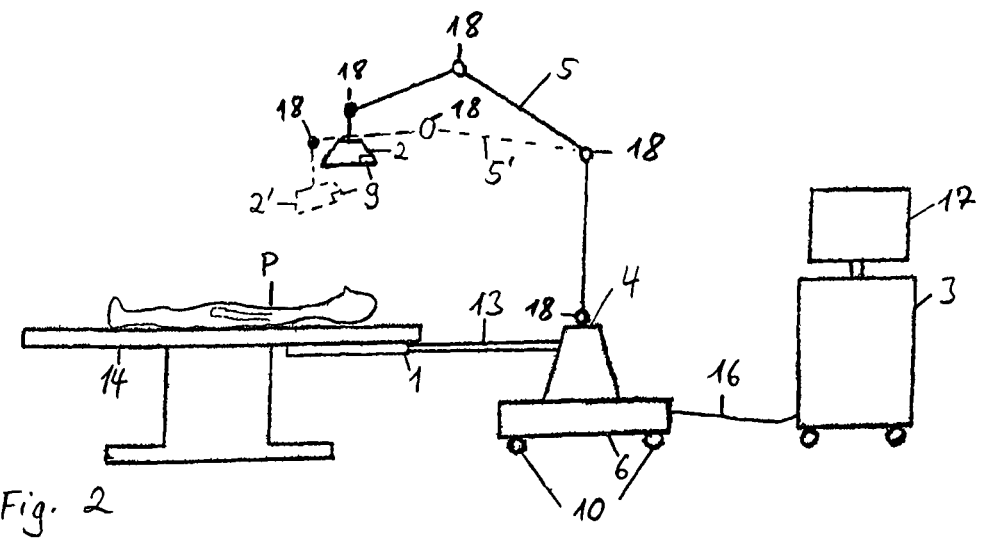
FIG. 2 is a schematic illustration of a side view of the X-ray system with a patient.

FIG. 2 shows a side view of an X-ray system, in which a patient P is located on the positioning unit 14. The calibration process has already been completed and the calibration body 15 has been removed. The radiation detector 1 is disposed beneath the positioning unit and mechanically and electrically connected to the stand 4 by way of an adapter 13. For reasons of greater stability, the adapter can be made of metal, or it can simply be made of plastic material, and it can accommodate the electrical connection 16 between the radiation detector 1 and the base 4. In the assembly shown, the positioning unit 14 is made of a material that allows X-rays to pass, for example plastic material. The stand base 6 is locally fixed by means of blockable wheels 10. So as to record multiple X-ray projection images, the stand arm 5 and the X-ray tube assembly 2 are displaced into differing positions 2' and 5', wherein the X-ray tube assembly 2' has been tilted as compared to the original orientation. The orientation and position of the X-ray tube assembly is defined by the joint positions of the stand arm. So as to increase the accuracy of the orientation determination, the X-ray tube assembly additionally contains a position sensor 9 in the exemplary embodiment shown. The position sensor 9 is an acceleration sensor, which detects the direction of gravitational acceleration as the reference direction and registers changes in the orientation relative thereto. As in FIG. 1, the stand 4 is connected to the control unit 3 and the display unit 17 via an electrical connection 16. The data can also be transmitted wirelessly by radio or infrared interfaces between the radiation detector, stand and control unit, and in this example only the power supply is provided via cables.

The device shown in FIGS. 1 and 2 is operated as follows: first, a calibration body 15 is introduced between the X-ray tube assembly 2 and radiation detector 1. At least one projection image of the calibration body 15 is created, from which a look-up table (LUT) is calculated, for example, as a calibration table and stored in a memory. Because the calibration body 15 is rigidly attached to the radiation detector 1, the recorded projection image can be used to clearly conclude the position and orientation of the X-ray tube assembly. The calibration step has to be carried out only once before each use and allows any arbitrary number of projection images to be recorded, as long as the stand 4 and the radiation detector 1 remain spatially fixed.

After the calibration body 15 is removed, the object to be represented is introduced in the position thereof. The X-ray tube assembly 2 is then displaced into specific relative positions, and a projection image is recorded in each of these relative positions. For the image reconstruction, each X-ray projection image, together with the coordinates of the X-ray tube assembly known from the calibration, can be used to reconstruct the scanned volume.

If necessary, it is also possible to displace the stand arm 5 out of the working range located above the positioning unit 14 and bring it back to the previous position using a motor so as to record further images.

For the movements into permanently identical relative positions, the radiation detector 2 is moved into these relative positions manually or driven by a motor by entering the coordinates in the control unit 3, and the coordinates are stored. Such a "teach-in" method predetermines exact relative positions by moving into them once, and the system can subsequently repeatedly move into these positions.

Figure 3:
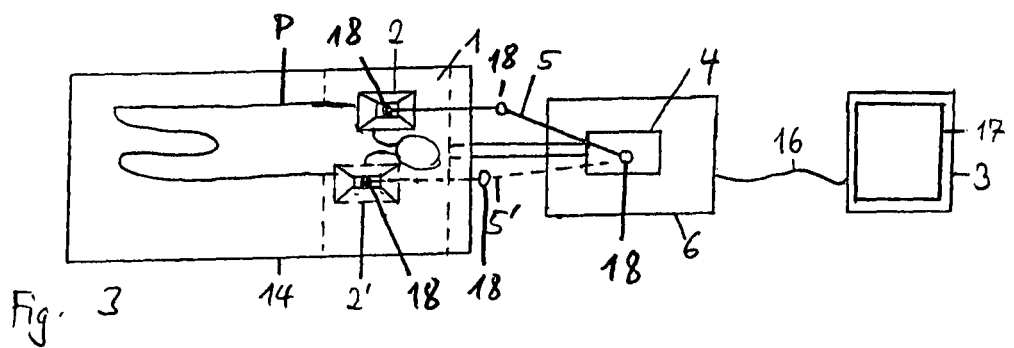
FIG. 3 is a top view of the X-ray system of FIG. 2.

FIG. 3 shows a top view of the X-ray system of FIG. 2 The radiation detector 1 has the same width as the positioning unit 14 so as to completely capture a patient P located thereon in the projection images. The stand arm 5 and the X-ray tube assembly 9 can be moved in all three spatial directions, as is shown based on positions 2' and 5'. The movement can be effected by way of several joints 18 that are attached to the stand arm 5. The X-ray tube assembly 2 can be moved in six degrees of freedom, three being translatory and three being rotatory. Instead of a patient P for medical use of X-rays, it is of course also possible to examine a different object with the system, for example as part of materials science analyses.

Figure 4A:
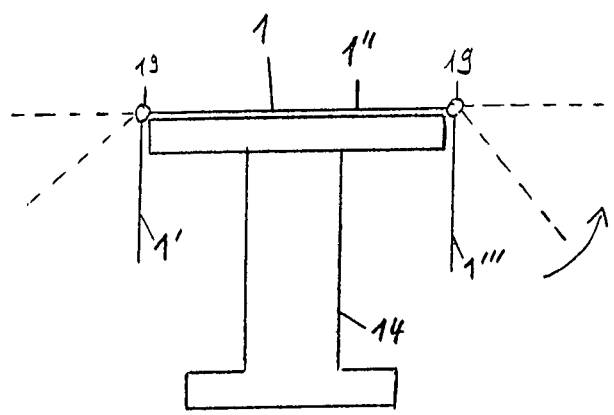
FIG. 4a shows a folding radiation detector.

A folding radiation detector 1 is shown in FIG. 4*a*. In this example, the radiation detector 1 is composed of a plurality of detector plates 1', 1", 1''', which are connected to each other by way of a mechanical coupling 19, such as a hinge or a joint. Each of the detector plates 1', 1", 1''' is composed of a detector having a scintillation layer, which, as described above, converts X-rays into visible light, wherein the visible light is detected on a pixel matrix. The detector plates 1', 1", 1''' are also electrically coupled via the respective connecting elements; as an alternative, separate electrical cables 16 can extend from each plate to the remaining system, however these are not shown for the sake of clarity. The radiation detector 1 rests on the positioning unit 14. The radiation detector 1 is extended to the maximum width thereof by folding out the detector plates 1', 1", 1''', and it is possible to record X-ray images in a larger angular range than when solely using the plate 1". If modifications are required to the object to be represented, which in the operating state rests on the radiation detector 1, the plates 1' and 1''' can be folded down so as to provide improved access. The movement of the plates is illustrated in FIG. 4*a* by the dotted lines.

Figure 4B:
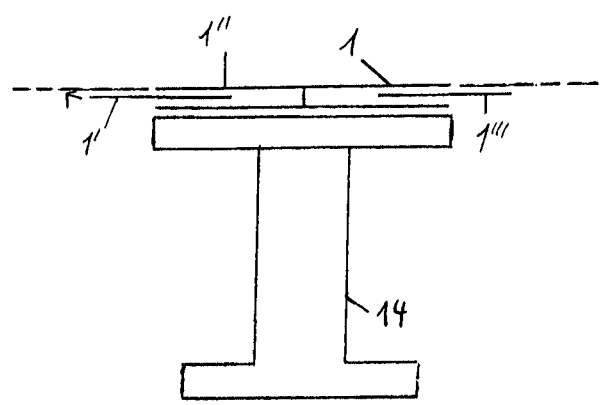
FIG. 4b shows a telescopic radiation detector.

FIG. 4*b* shows a radiation detector 1 having telescopic detector plates 1', 1", 1'''. If they are not needed, the plates 1' and 1''' can be lowered beneath the plate 1", whereby the radiation detector 1 forms a compact unit that is easy to transport. The radiation detector 1 again rests on the positioning unit 14, but can be easily removed therefrom. The extended positions of the plates 1' and 1''' are again shown by dotted lines. In this embodiment, the individual plates 1', 1", 1''' are also mechanically and electrically in contact with each other. If the electrical contact does not exist, electrical connections 16, which are not shown here, lead to the stand 4 and/or the control unit.

The invention claimed is:

1. An X-ray system for generating 3D image data, comprising:
   a radiation detector,
   a movable X-ray tube assembly and a control unit,
   wherein in a working state of the system the radiation detector is detachably positioned in a spatially fixed manner and defines a locally fixed base coordinate system, and the X-ray tube assembly is movable relative to the radiation detector into different relative positions so as to record X-ray projection images,
   wherein projection images recorded in the relative positions, combined with the coordinates of the relative positions, are processable using an iterative reconstruction technique or other image processing methods to obtain 3D X-ray images, and
   wherein the system comprises a movable stand having a motor-driven movable stand arm and a stand base,
   wherein the X-ray tube assembly is attached to the stand arm and is movable in at least four degrees of freedom, and the stand base comprises fastening devices for the spatially fixed positioning and, in the working state, is positioned in a spatially fixed manner such that it has a defined fixed position within the base coordinate system, and the stand arm is displaceable into the relative position by way of the control unit,
   wherein the stand base comprises one or more sensors for ensuring that a spatially fixed position of the stand base is maintained.

2. The X-ray system according to claim 1, further comprising one or more additional sensors for monitoring particular areas for the presence of people during an X-ray recording procedure, which transmit a signal to the control unit so as to interrupt the X-ray recording if people are present.

3. The X-ray system according to claim 1, characterized in that the one or more sensors comprise lasers.

4. An X-ray system according to claim 1, characterized in that the X-ray tube assembly is movable in at least five degrees of freedom.

5. An X-ray system according to claim 1, further comprising one or more position sensors for determining the relative position of the X-ray tube assembly with respect to the base coordinate system.

6. An X-ray system according to claim 1, characterized in that the fastening devices comprise blockable wheels or a vacuum suction system for positioning the stand base in the spatially fixed manner.

7. An X-ray system according to claim 1, characterized in that the radiation detector is detachably positionable in a spatially fixed manner by holding devices.

8. An X-ray system according to claim 1, characterized in that the stand arm is movable manually.

9. An X-ray system according to claim 1, characterized in that the radiation detector is mechanically connected to the stand by way of an adapter.

10. An X-ray system according to claim 1, characterized in that a positioning unit is present, the positioning unit and the radiation detector having substantially the same width.

11. An X-ray system according to claim 1, characterized in that the radiation detector is designed as a folding or telescopic multi-component system comprising a plurality of individual detector plates.

12. A method for using an X-ray system according to claim 1, comprising the following steps:
   a) calibrating the system, with the radiation detector being spatially fixed and the stand base being spatially fixed, by means of a calibration body which is located between the X-ray tube assembly and radiation detector, wherein at least one X-ray projection image of the calibration body is recorded;
   b) recording X-ray projection images of an object to be represented which is located between the X-ray tube assembly and the radiation detector; and
   c) calculating a 3D reconstruction of a scanned volume of the object by using the iterative reconstruction technique or the other image processing methods based on the X-ray projection images of the object to be represented and the coordinates of the relative positions used for the recording.

13. The method according to claim 12, characterized in that the motor-driven movable stand arm is provided with predetermined relative positions that are located on a recording track for recording X-ray projection images by way of a "teach-in" method, and the control unit can automatically move to the relative positions of this recording track.

14. The method according to claim 13, characterized in that on a recording track predetermined by a "teach-in" method, the optimal recording positions of the X-ray tube assembly on the recording track are calculated by evaluating a predefined number of X-ray projection images of the object to be represented, and the control unit moves to these calculated optimal relative positions for future recordings.

* * * * *